(12) United States Patent
Marshall

(10) Patent No.: US 7,465,289 B2
(45) Date of Patent: Dec. 16, 2008

(54) SYRINGE FIRING MECHANISM

(75) Inventor: Jeremy Marshall, Oxford (GB)

(73) Assignee: Owen Mumford Limited, Oxfordshire (GB)

( * ) Notice: Subject to any disclaimer, the term of this patent is extended or adjusted under 35 U.S.C. 154(b) by 128 days.

(21) Appl. No.: 10/559,179

(22) PCT Filed: May 25, 2004

(86) PCT No.: PCT/GB2004/002248

§ 371 (c)(1),
(2), (4) Date: Feb. 24, 2006

(87) PCT Pub. No.: WO2004/108194

PCT Pub. Date: Dec. 16, 2004

(65) Prior Publication Data

US 2006/0167412 A1  Jul. 27, 2006

(30) Foreign Application Priority Data

Jun. 5, 2003 (GB) ................................. 0312852.7

(51) Int. Cl.
*A61M 5/20* (2006.01)
(52) U.S. Cl. ...................................... 604/136
(58) Field of Classification Search ................ 604/110, 604/131, 132, 134–136, 151, 187, 195–198; 128/919

See application file for complete search history.

(56) References Cited

U.S. PATENT DOCUMENTS

| 3,702,608 | A | * | 11/1972 | Tibbs | ........................ 604/136 |
| 5,137,516 | A | | 8/1992 | Rand et al. | |
| 5,300,030 | A | * | 4/1994 | Crossman et al. | ........... 604/136 |
| 5,599,309 | A | * | 2/1997 | Marshall et al. | ............. 604/136 |
| 5,779,677 | A | | 7/1998 | Frezza | |
| 6,099,503 | A | * | 8/2000 | Stradella | ...................... 604/135 |
| 6,159,181 | A | * | 12/2000 | Crossman et al. | ........... 604/157 |
| 6,270,479 | B1 | * | 8/2001 | Bergens et al. | .............. 604/156 |
| 6,371,939 | B2 | * | 4/2002 | Bergens et al. | .............. 604/156 |
| 6,805,686 | B1 | * | 10/2004 | Fathallah et al. | ............ 604/135 |
| 6,932,793 | B1 | * | 8/2005 | Marshall et al. | ............. 604/135 |
| 7,066,907 | B2 | * | 6/2006 | Crossman et al. | ........... 604/110 |

FOREIGN PATENT DOCUMENTS

EP       0 516 473       12/1992

\* cited by examiner

*Primary Examiner*—Nicholas D Lucchesi
*Assistant Examiner*—Aarti Bhatia
(74) *Attorney, Agent, or Firm*—Young & Thompson

(57) ABSTRACT

When a cover (10) of a syringe firing mechanism is pushed downwardly towards a housing (2) a flexible arm (12) is moved inwardly to release a trigger (8). This enables a drive member (6) to push down a plunger (5) of the syringe under the bias of a spring (7). When the injection is completed, release of the cover (10) causes the cover (10) to move back into contact with a corner of the drive member (6). A cam surface (15A) then pushes a flap (16) across, whilst bending a hinge (17), until the flap (16) enters the hollow interior of the drive member (6), thus enabling the syringe (1) to be withdrawn within the housing (2) under the bias of a spring (3).

20 Claims, 4 Drawing Sheets

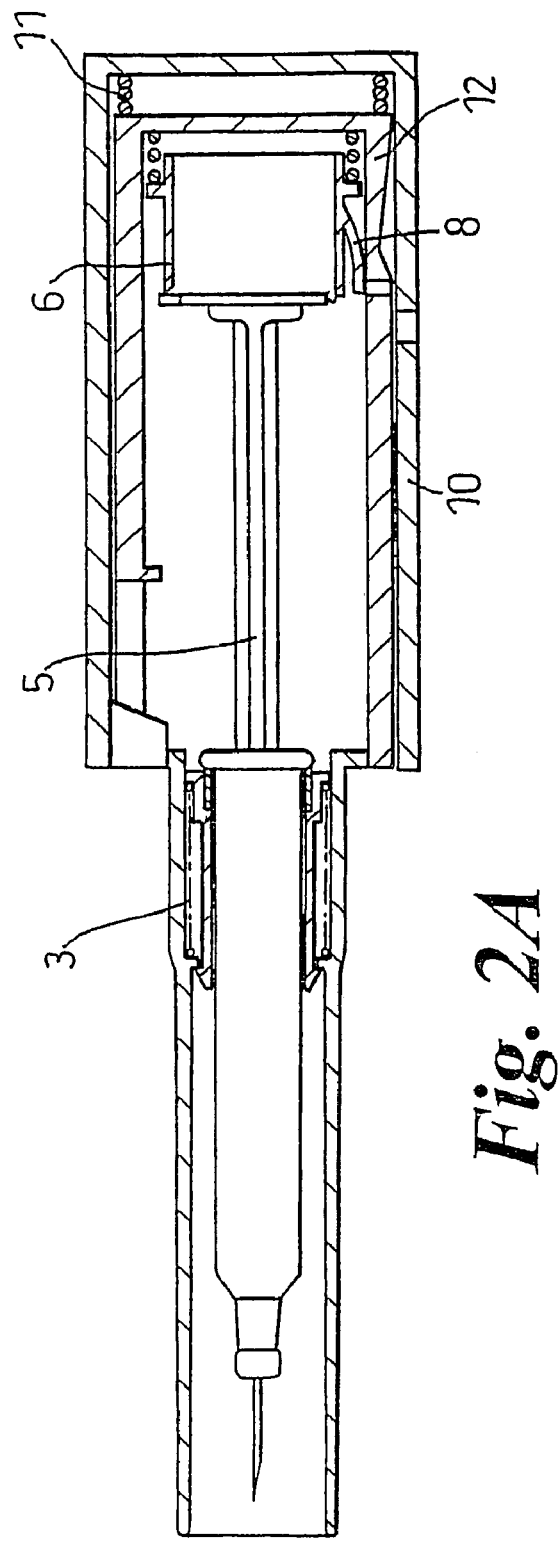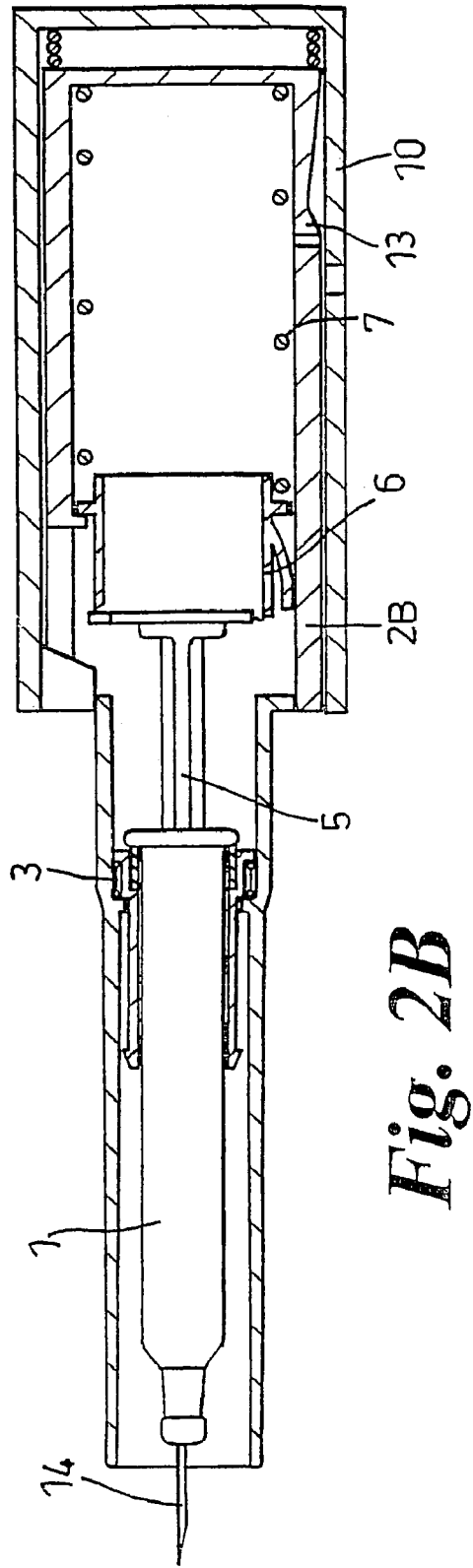
Fig. 2A
Fig. 2B

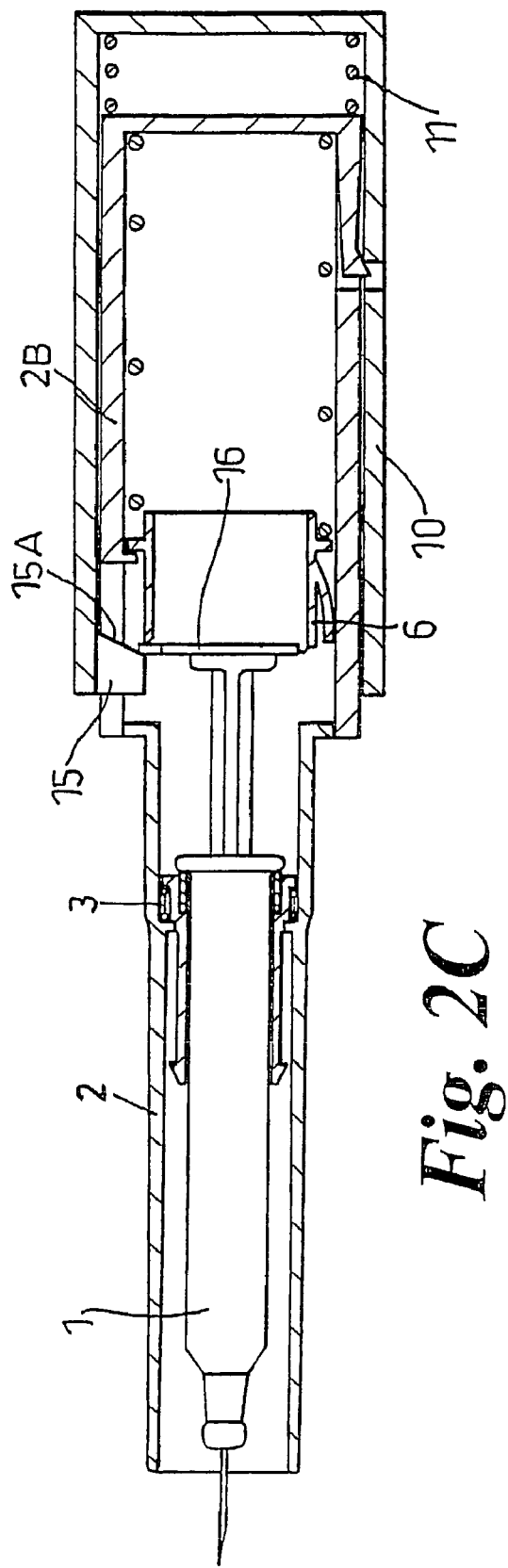
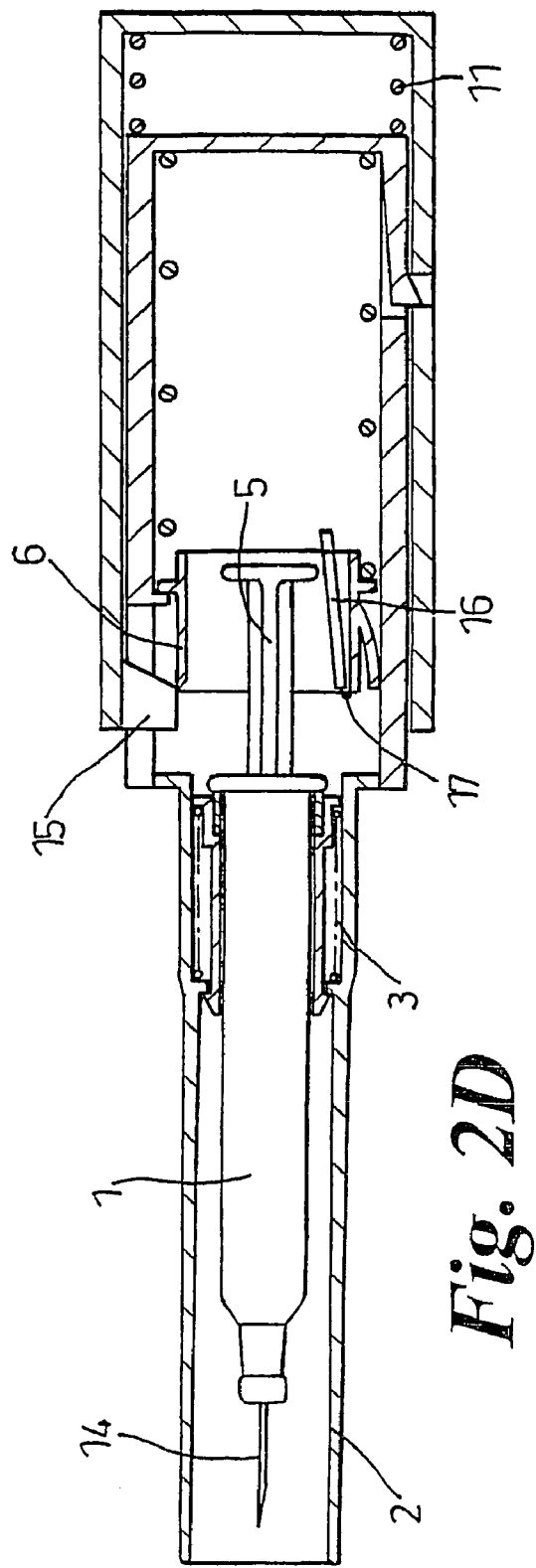

SYRINGE FIRING MECHANISM

BACKGROUND OF THE INVENTION

Safety syringe mechanisms are known wherein the syringe is initially held fully within a housing and, after injection, the syringe is again drawn back into the housing. Such arrangements usually have a drive member which can be released and driven forward, firstly to cause the needle at least of the syringe to project from the housing, and then to cause a dose to be ejected from the syringe through the enclosed needle. At the end of the injection procedure, the syringe is caused to be withdrawn again into the housing by a return mechanism. This invention aims to provide a syringe firing mechanism of this nature which is relatively simple in construction and which can readily be operated to perform the two stages of exposing the needle of the syringe and withdrawing the syringe into a housing after injection.

SUMMARY OF THE INVENTION

According to the present invention there is provided a syringe firing mechanism for a syringe held within a housing, the housing incorporating a drive spring acting on a drive member provided with a release trigger which, when released, enables the drive member to act on a plunger of the syringe under the bias of the drive spring, firstly to drive the body of the syringe forwardly to cause the needle portion of the syringe to move out of the housing and secondly to cause a dose to be ejected from the syringe, the housing also incorporating a return spring to provide a reverse bias on the syringe body to enable the needle portion of the syringe to be withdrawn into the housing after ejection of a dose, and a cover positioned over the rear of the housing and movable in a first direction towards the syringe to actuate the release trigger or to provide access for actuation of the release trigger, and movable subsequently in the reverse direction to actuate a release mechanism which will free the plunger from the drive member to allow the syringe to be withdrawn into the housing under the bias of the return spring.

With this mechanism the cover acts firstly to release the drive member and then to actuate a further release mechanism which causes the exposed needle to be withdrawn back into the housing. In the preferred arrangement, the release mechanism comprises a projection inwardly from the region of the cover nearest to the syringe which will, when the cover is moved in the reverse direction, release a flap on the drive member to enable the head of the syringe plunger to enter a hollow interior of the drive member.

Ideally a third spring will be provided between the cover and the housing to cause the cover to move back to its start position, to actuate the release mechanism, when the operator's actuating pressure on the cover is released. This ensures that the operation of the release mechanism happens automatically once the operator releases the device.

In the preferred arrangement, the drive head will carry the release trigger which is normally located on a ledge of the housing until it is moved off the ledge, for release of the trigger to enable the drive member to move within the housing under the bias of the drive spring. In one arrangement, the structure is such that movement of the cover in the first direction pushes the trigger off the ledge. In this case, the housing can have a flexible arm whose free end contacts the release trigger and also carries a projection which will be moved inwardly by movement of the cover in the first direction to any extent sufficient to actuate the release trigger.

As an alternative, the firing mechanism could be constructed such that there is a firing button, for actuating the release trigger, which projects through a side wall of the cover and is interlocked with the cover until the cover is moved in the first direction, whereupon the button can be pressed to actuate the release trigger. The firing button can be carried at the end of a flexible arm forming part of the housing.

BRIEF DESCRIPTION OF THE DRAWINGS

The invention may be performed in various ways and two preferred embodiments thereof will now be described, with reference to the accompanying diagrammatic drawings, in which:

FIGS. 2A to 2D illustrate sequential stages of operation of the mechanism shown in FIG. 1.

DESCRIPTION OF THE PREFERRED EMBODIMENTS

Figure 1:
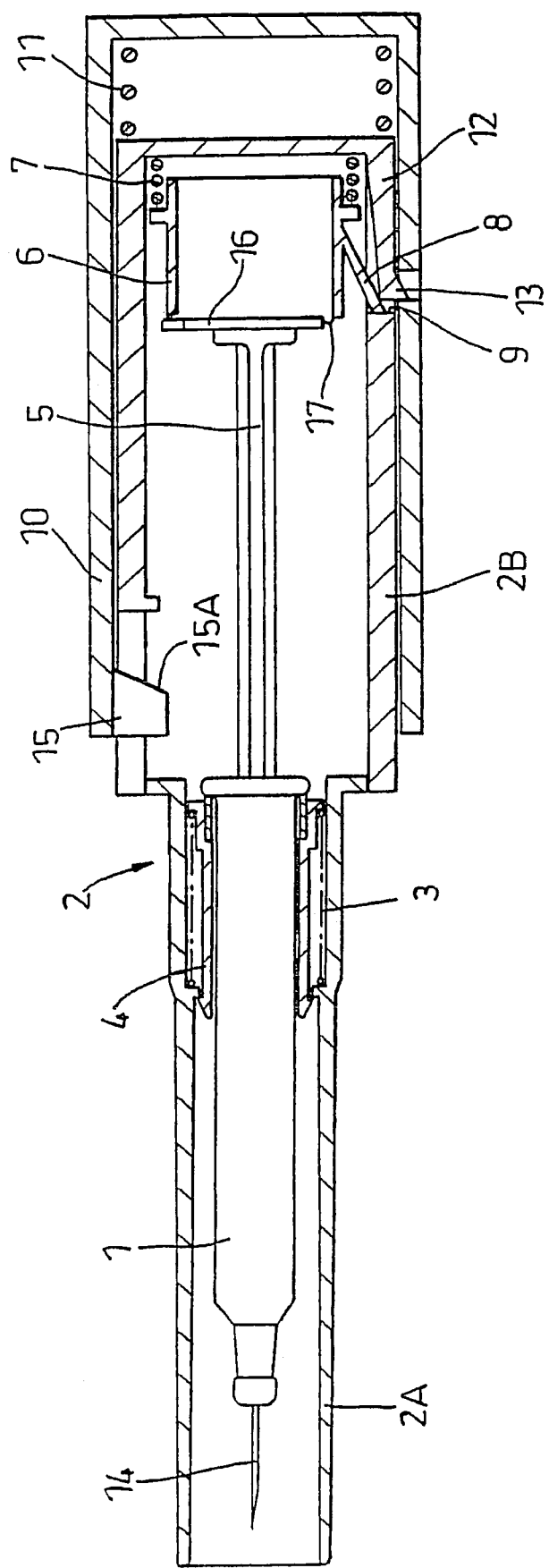
FIG. 1 is a longitudinal cross-section through one example of a syringe firing mechanism of this invention.

FIG. 1 shows a standard syringe 1 located within a housing 2. A spring 3 biases a syringe carrier 4 associated with the syringe in a direction such as to hold the syringe 1 fully within the lower part of the housing 2A. A plunger 5 projects from the syringe 1 into the upper part 2B of the housing. At the top end of the housing section 2B there is a drive member 6 biased by a drive spring 7. The drive member is held in place by a trigger 8 in the form of a flexible arm which rests on a ledge 9 in an opening in the side wall of the housing 2.

Surrounding the upper part of the housing 2B is a cover 10 which is biased outwardly by a spring 11. If the operator pushes the cover 10 towards the syringe 1, a flexible arm 12 of the housing 2 is forced inwardly by engagement of the inner side wall of the cover 10 with a projecting boss 13 on the arm 12 until the condition is reached as shown in FIG. 2B. The drive member 6 is now free to move within the housing portion 2B under the bias of the spring 7 and acts on the plunger 5 initially to cause the syringe 1 to move outwardly against the bias of the weaker spring 3 and then to cause the contents of the syringe to be ejected through the needle 14 as the plunger moves within the syringe 1. When the cover 10 is subsequently released, the spring 11 acts to move the cover 10 outwardly. This results in a trigger member 15 acting on a flap 16 forming part of the drive member 6 (as shown in FIG. 2C). Further movement of the trigger member 15 to the position shown in FIG. 2D causes the flap 16 to disengage from the side wall of the drive member 6. This results from the fact that the cam surface 15A pushes the flap 16 across by flexing a hinge 17 until the flap enters the interior of the hollow drive member 6. The flap 16 can then fold inwardly about the hinge 17 into the interior of the hollow drive member 6. This removes any pressure from the plunger 5 and the spring 3 acts to withdraw the syringe 1 back into the housing 2.

Figure 3A:
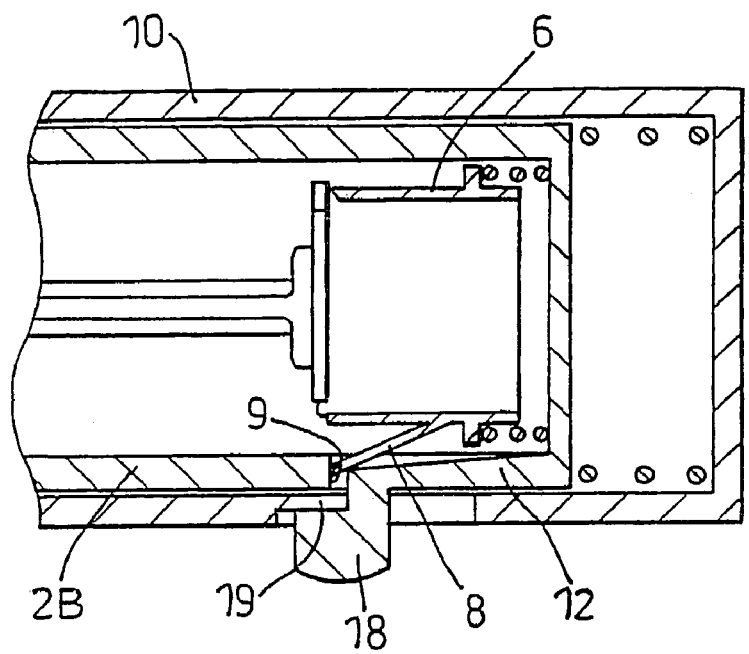
FIGS. 3A and 3B illustrate, in partial view and in a similar manner, two initial stages in the operation of an alternative form of firing mechanism.
Figure 3B:
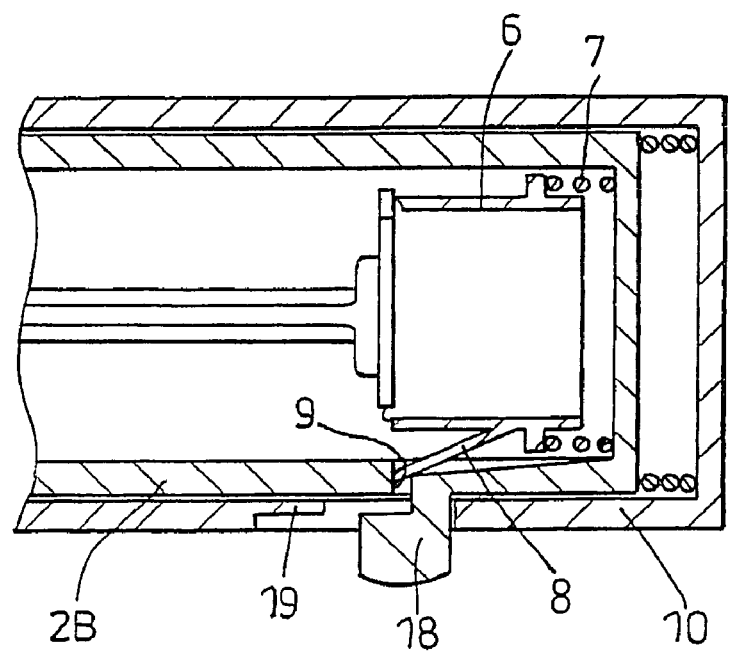

In the alternative arrangement shown in FIGS. 3A and 3B, the closing inwardly of the trigger 8 of the drive member 6 is performed in a different manner. Otherwise, the operation of the device is identical to that shown in FIGS. 1 and 2. In this instance, the flexible arm 12 of the housing portion 2B extends outwardly at the free end to form a button 18. In the condition shown in FIG. 3A, this button cannot be moved inwardly because it rests against a portion 19 of the cover 10.

However, when the cover 10 is moved inwardly to the condition shown in FIG. 3B (corresponding essentially to that shown in FIG. 2A), the button 18 is free to move inwardly, when pressed, to move the latch inwardly to free it from the ledge 9. Again, the drive member 6 can then be driven with forward by the spring 7 and the subsequent stages of operation are equivalent to those shown in FIGS. 2B to 2D.

The invention claimed is:

1. A syringe firing mechanism for a syringe held within a housing, the housing incorporating a drive spring acting on a drive member provided with a release trigger which, when released, enables the drive member to act on a plunger of the syringe under the bias of the drive spring, firstly to drive the body of the syringe forwardly to cause the needle portion of the syringe to move out of the housing and secondly to cause a dose to be ejected from the syringe, the housing also incorporating a return spring to provide a reverse bias on the syringe body to enable the needle portion of the syringe to be withdrawn into the housing after ejection of a dose, and a cover positioned over the rear of the housing, which moves in a first direction towards the syringe to actuate the release trigger or to provide access for actuation of the release trigger, and which moves subsequently in the reverse direction and actuates a release mechanism which will free the plunger from the drive member to allow the syringe to be withdrawn into the housing under the bias of the return spring.

2. A syringe firing mechanism according to claim 1, wherein said release mechanism comprises a projection inwardly from the region of the cover nearest to the syringe which will, when the cover is moved in the reverse direction, release a flap on the drive member to enable the head of the syringe plunger to enter a hollow interior of the drive member.

3. A syringe firing mechanism according to claim 1, wherein a third spring is provided between the cover and the housing to cause the cover to move back to its start position, to actuate the release mechanism, when the operator's actuating pressure on the cover is released.

4. A syringe firing mechanism according to claim 1, wherein a drive head carries the release trigger which is normally located on a ledge of the housing until it is moved off the ledge, for release of the trigger to enable the drive member to move within the housing under the bias of the drive spring.

5. A syringe firing mechanism according to claim 4, wherein movement of the cover in the first direction pushes the trigger off the ledge.

6. A syringe firing mechanism according to claim 5, wherein the housing has a flexible am whose free end contacts the release trigger and also carries a projection which will be moved inwardly by movement of the cover in the first direction to any extent sufficient to actuate the release trigger.

7. A syringe firing mechanism according to claim 4, wherein a firing button for actuating the release trigger projects through a side wall of the cover and is interlocked with the cover until the cover is moved in the first direction, whereupon the button can be pressed to actuate the release trigger.

8. A syringe firing mechanism according to claim 7, wherein the firing button is carried at the end of a flexible arm forming part of the housing.

9. A syringe firing mechanism according to claim 2, wherein a third spring is provided between the cover and the housing to cause the cover to move back to its start position, to actuate the release mechanism, when the operator's actuating pressure on the cover is released.

10. A syringe tiring mechanism according to claim 2, wherein a drive head carries the release trigger which is normally located on a ledge of the housing until it is moved off the ledge, for release of the trigger to enable the drive member to move within the housing under the bias of the drive spring.

11. A syringe firing mechanism according to claim 3, wherein a drive head carries the release trigger which is normally located on a ledge of the housing until it is moved off the ledge, for release of the trigger to enable the drive member to move within the housing under the bias of the drive spring.

12. A syringe firing mechanism for a syringe, comprising:
a housing within which housing a syringe is located, the syringe including a plunger projecting from the syringe into an upper part of the housing, and a needle,
the housing comprising i) a side wall, ii) an opening in the side wall, the opening defining a ledge, and iii) a flexible arm located at the opening, the flexible arm including a projecting boss;
a syringe carrier inside a lower part of the housing;
a first spring biasing the syringe carrier in a direction to hold the syringe fully within the lower part of the housing;
a drive member located within the upper part of the housing and including i) a flap connected to a side wall of the drive member, and ii) a trigger;
a drive spring biasing the drive member, the drive spring located at the top end of the upper part of the housing;
the trigger holding the drive member in place, the trigger including a flexible arm resting on the ledge of the opening in the side wall of the housing;
a cover surrounding the upper part of the housing;
a third spring located interior to the cover and outwardly biasing a hop end of the cover; and
a trigger member located at a bottom end of the cover, wherein,
pushing the cover towards the syringe forces the flexible arm of the housing inwardly by engagement of an inner side wall of the cover with the projecting boss of the arm and causes the flexible arm of the trigger to move inwardly off the ledge and reward the drive member to free the drive member to move within the upper part of the housing under the bias of the drive spring, the drive member acting on the plunger initially to cause the syringe to move outwardly against the bias of the first spring and then to cause contents of the syringe to be ejected through the needle as the plunger moves within the syringe,
subsequent release to the cover results in the third spring acting to move the cover outwardly, the cover moving outwardly resulting in the trigger member moving to act on the flap of the drive member and disengage the flap from the side wall of the drive member, and
subsequent to the flap disengaging from the side wall of the drive member, the first spring acting to withdraw the syringe back into the housing.

13. The syringe firing mechanism of claim 12, wherein,
the drive member is hollow and includes an interior;
the trigger member comprises a cam surface;
the flap includes a hinge connecting the flap to the side wall of the drive member, and
the disengaging of the flap from the side wall of the drive member is caused by the cam surface pushing the flap across by flexing the hinge until the flap enters the interior of the drive member, the flap folding inwardly about the hinge into the interior of the drive member.

14. A syringe firing mechanism for a syringe, comprising:
a housing within which housing a syringe is located, the syringe including a plunger projecting from the syringe into an upper part of the housing, and a needle,
the housing comprising i) a side wall, ii) an opening in the side wall, the opening defining a ledge, and iii) a flexible arm located at the opening, the flexible arm including a projecting element;
a syringe carrier inside the housing;
a first spring biasing the syringe carrier in a direction to hold the syringe fully within a lower part of the housing;
a drive member located within a top end of the upper part of the housing and including a flap disengagably connected to a side wall of the drive member;
a drive spring biasing the drive member, the drive spring located at the top end of the upper part of the housing;
a trigger holding the drive member in place, the trigger including a flexible arm resting on the ledge of the opening in the side wall of the housing;
a cover surrounding the upper part of the housing;
a trigger member located at a bottom end of the cover, wherein,
pushing the projecting element of the flexible arm of the housing inwardly causes the flexible arm of the trigger to move inwardly off the ledge and toward the drive member to free the drive member to move within the upper part of the housing under the bias of the drive spring, the drive member acting on the plunger initially to cause the syringe to move outwardly against the bias of the first spring and then to cause contents of the syringe to be ejected through the needle as the plunger moves within the syringe,
subsequent release of the cover results in the cover moving outwardly, the cover moving outwardly resulting in the trigger meter moving to act on the flap of the drive member and disengage the flap from the aide wall of the drive member, and
subsequent to the flap disengaging from the side wall of the drive member, the first spring acting to withdraw the syringe back into the housing.

15. The syringe firing mechanism of claim 14, wherein,
the projecting element is a projecting boss, and
pushing the cover towards the syringe forces the flexible arm of the housing inwardly by engagement of an inner side wall of the cover with the projecting boss of the arm and causes the flexible arm of the trigger to move inwardly off the ledge and toward the drive member to free the drive member to move within the upper part of the housing under the bias of the drive spring.

16. The syringe firing mechanism of claim 14, wherein,
the projecting element is a projecting button, and
pushing the projecting button of the flexible arm of the housing inwardly pushes the flexible arm of the trigger to move inwardly off the ledge and toward the drive member to free the drive member to move within the upper part of the housing under the bias of the drive spring, the drive member acting on the plunger initially to cause the syringe to move outwardly against the bias of the first spring and then to cause contents of the syringe to be ejected through the needle as the plunger moves within the syringe.

17. The syringe firing mechanism of claim 16, wherein,
in an initial position, the button rests against a portion of the cover and cannot be moved inwardly, and
moving the cover inwardly from the initial position to another position frees the button from resting against the portion of the cover and allows the button to be moved inwardly against the flexible arm of the trigger.

18. The syringe firing mechanism of claim 16, further comprising:
a second spring located interior to the cover and outwardly biasing a top end of the cover, wherein,
the subsequent release of the cover results in the second spring acting to move the cover outwardly, the cover moving outwardly resulting in the trigger member moving to act on the flap of the drive member and disengage the flap from the side wall of the drive member.

19. The syringe firing mechanism of claim 18, wherein,
the drive member is hollow and includes an interior;
the trigger member comprises a cam surface;
the flap includes a hinge connecting the flap to the side wall of the drive member, and
the subsequent release of the cover that results in the second spring acting to move the cover outwardly with the cover moving outwardly resulting in the trigger member moving to act on the flap of the drive member and disengage the flap from the side wall of the drive member, causes the cam surface to push the flap across by flexing the hinge until the flap enters the interior of the drive member, the flap folding inwardly about the hinge into the interior of the drive member.

20. The syringe firing mechanism of claim 14, wherein,
the drive member is hollow and includes an interior;
the trigger member comprises a cam surface;
the flap includes a hinge connecting the flap to the side wall of the drive member, and
the subsequent release of the cover that results in the cover moving outwardly with the cover moving outwardly resulting in the trigger member moving to act on the flap of the drive member and disengage the flap from the side wall of the drive member, causes the cam surface to push the flap across by flexing the hinge until the flap enters the interior of the drive member, the flap folding inwardly about the hinge into the interior of the drive member.

* * * * *